(12) United States Patent
Padoy et al.

(10) Patent No.: US 11,224,386 B2
(45) Date of Patent: Jan. 18, 2022

(54) METHOD FOR DETERMINING A CONFIGURATION SETTING OF A SOURCE OF IONIZING RADIATION

(71) Applicants: UNIVERSITE DE STRASBOURG, Strasbourg (FR); CENTRE NATIONAL DE LA RECHERCHE SCIENTIFIQUE—CNRS-, Paris (FR)

(72) Inventors: Nicolas Padoy, Strasbourg (FR); Nicolas Loy Rodas, Strasbourg (FR); Michel de Mathelin, Strasbourg (FR); Julien Bert, Brest (FR); Dimitris Visvikis, Brest (FR)

(73) Assignees: UNIVERSITE DE STRASBOURG, Strasbourg (FR); CENTRE NATIONAL DE LA RECHERCHE SCIENTIFIQUE—CNRS-, Paris (FR)

( * ) Notice: Subject to any disclaimer, the term of this patent is extended or adjusted under 35 U.S.C. 154(b) by 0 days.

(21) Appl. No.: 16/481,590

(22) PCT Filed: Jan. 29, 2018

(86) PCT No.: PCT/EP2018/052101
§ 371 (c)(1),
(2) Date: Jul. 29, 2019

(87) PCT Pub. No.: WO2018/141680
PCT Pub. Date: Aug. 9, 2018

(65) Prior Publication Data
US 2020/0000418 A1    Jan. 2, 2020

(30) Foreign Application Priority Data

Jan. 31, 2017 (EP) .................................... 17305111

(51) Int. Cl.
A61B 6/10 (2006.01)
A61B 6/00 (2006.01)
A61N 5/10 (2006.01)

(52) U.S. Cl.
CPC ............ *A61B 6/107* (2013.01); *A61B 6/4441* (2013.01); *A61B 6/542* (2013.01); *A61B 6/547* (2013.01); *A61N 5/1048* (2013.01)

(58) Field of Classification Search
None
See application file for complete search history.

(56) References Cited

U.S. PATENT DOCUMENTS 5,077,685 A    12/1991 Iwashima et al.
9,517,044 B2 *  12/2016 Bouvier ................. A61B 6/547
(Continued)

FOREIGN PATENT DOCUMENTS

EP    2 465 435 A1    6/2012
JP    2000-152924 A    6/2000
(Continued)

OTHER PUBLICATIONS

Agostinelli et al., "Geant4—a simulation toolkit," Nuclear Instruments and Methods in Physics Research Section A Accelerators, Spectrometers, Detectors and Associated Equipment, 2003, vol. 506, No. 3, pp. 250-303.
(Continued)

*Primary Examiner* — Andrew Smyth
(74) *Attorney, Agent, or Firm* — Faegre Drinker Biddle & Reath LLP

(57) ABSTRACT

A method for determining a configuration setting of a source of ionizing radiation reducing a radiation dose absorbed by a patient and a practitioner in a medical operating room during a procedure. Prior to the procedure a database of maps of simulated propagation and scattering of ionizing
(Continued)

radiation in a model of the medical operating room is obtained for different configuration settings. During the procedure, a position of the practitioner is determined. After determining a set of configuration settings of the source enabling the production of an image of a target anatomical structure a radiation dose absorbed by the patient and the practitioner is determined using the maps from the database. A recommended configuration setting for which a combined radiation dose is reduced is then outputted.

15 Claims, 6 Drawing Sheets

(56) References Cited

U.S. PATENT DOCUMENTS

| | | | |
|---|---|---|---|
| 2010/0127859 A1* | 5/2010 | Hohmann | A61N 5/1048 340/540 |
| 2012/0148131 A1 | 6/2012 | Couch et al. | |
| 2013/0003915 A1 | 1/2013 | Lautenschlager et al. | |
| 2013/0048883 A1 | 2/2013 | Simon et al. | |
| 2014/0095117 A1* | 4/2014 | Vainshtain | G06F 30/20 703/1 |
| 2015/0063545 A1* | 3/2015 | Lee | G16H 30/40 378/91 |
| 2015/0100290 A1* | 4/2015 | Fait | A61N 5/1075 703/2 |
| 2016/0166854 A1* | 6/2016 | Bharat | A61N 5/1037 600/1 |

FOREIGN PATENT DOCUMENTS

| | | |
|---|---|---|
| JP | 2000-221292 A | 8/2000 |
| JP | 2004-065815 A | 3/2004 |
| WO | 2008/104915 A2 | 9/2008 |
| WO | 2013/088308 A1 | 6/2013 |
| WO | 2014/052786 A2 | 4/2014 |
| WO | 2015/054314 A1 | 4/2015 |
| WO | 2016/020278 A1 | 2/2016 |

OTHER PUBLICATIONS

Beasley, "Medical robots: Current systems and research directions," Journal of Robotics, 2012, Hindawi Publishing Corp., vol. 2012, 14 pages.

Bert et al., "Geant4-based Monte Carlo simulations on GPU for medical applications," Physics in Medicine and Biology, 2013, IOP Publishing, vol. 58, No. 16, pp. 5593-5611.

Bert et al., "Ggems: GPU Geant4-based Monte Carlo Simulation platform," IEEE Nuclear Science Symposium and Medical Imaging Conference, 2016, pp. 69-71.

Fallavollita et al., "Desired-View -Controlled Positioning of Angiographic C-arms," Medical Image Computing and Computer Assisted Intervention—MICCAI, 2014, pp. 659-666.

Farzan et al., "From D-H to Inverse Kinematics: A Fast Numerical Solution for General Robotic Manipulators Using Parallel Processing," 2013 IEEE/RSJ International Conference on Intelligent Robots and Systems (IROS), Tokyo, Japan, 2013, pp. 2507-2513.

Kadkhodamohammadi et al., "Articulated Clinician Detection Using 3D Pictorial Structures on RGB-D Data," Medical Image Analysis, 2017, vol. 35, pp. 215-224.

Kirkwood et al., "Radiation-induced skin injury after complex endovascular procedures," Journal of Vascular Surgery, 2014, vol. 60, No. 3, pp. 742-748.

Klaser et al., "A Spatio-Temporal Descriptor Based on 3D-Gradients," Proceedings of the 19th British Machine Mision Conference, 2008, pp. 1-10.

Koukorava et al., "Study of the parameters affecting operator doses in interventional radiology using Monte Carlo simulations," Radiation Measurements, 2011, vol. 46, No. 11, pp. 1216-1222.

Loy Rodas et al., "See It Wth Your Own Eyes: Marker-less Mobile Augmented Reality for Radiation Awareness in the Hybrid Room," IEEE Transactions on Biomedical Engineering, 2016, vol. 62, No. 2, pp. 429-440.

Loy Rodas et al., "Augmented Reality for Reducing Intraoperative Radiation Exposure to Patients and Clinicians During X-Ray Guided Procedures," Mixed and Augmented Reality in Medicine, 2018, CRC Press, pp. 217-229.

Loy Rodas et al., "Pose optimization of a C-arm imaging device to reduce intraoperative radiation exposure of staff and patient during interventional procedures," 2017 IEEE International Conference on Robotics and Automation (ICRA), 2017, pp. 4200-4207.

National Council On Radiation Protection and Measurements, "NCRP, Report No. 107—Implementation of the Principle of As Low As Reasonably Achievable (ALARA) for Medical and Dental Personnel", National Council on Radiation Protection and Measurements, 1990, Abstract.

Navab et al., "Visual Servoing for Intraoperative Positioning and Repositioning of Mobile C-arms," Medical Image Computing and Computer-Assisted Intervention—MICCAI, 2006, pp. 551-560.

Nikodemova et al., "Staff extremity doses in interventional radiology. Results of the ORAMED measurement campaign," Radiation Measurements, 2011, vol. 46, No. 11, pp. 1210-1215.

Piccin et al., "A Force Feedback Teleoperated Needle Insertion Device for Percutaneous Procedures," The International Journal of Robotics Research, 2009, vol. 28, No. 9, pp. 1154-1168.

Roguin et al., "Brain and Neck Tumors Among Physicians Performing Interventional Procedures," The American Journal of Cardiology, 2013, vol. 111, No. 9, pp. 1368-1372.

Schueler et al., "An Investigation of Operator Exposure in Interventional Radiology," RadioGraphics, Oct. 2006, vol. 26, No. 5, pp. 1533-1541.

Tornai et al., "Fast DRR generation for 2Dto 3D registration on GPUs," Medical Physics, Aug. 2012, vol. 39, No. 8, pp. 4795-4799.

Wang et al., "Closed-Form Inverse Kinematics for Interventional C-Arm X-Ray Imaging With Six Degrees of Freedom Modeling and Application," IEEE Transactions on Medical Imaging, May 2012, vol. 31, No. 5, pp. 1086-1099.

Wang et al., "Optimal Viewing Angle Determination for Multiple Vessel Segments in Coronary Angiographic Image," EEE Transactions on Nuclear Science, Jun. 2014, vol. 61, No. 3, pp. 1290-1303.

Zhang et al., "Parameterization of brachytherapy source phase space file for Monte Carlo-based clinical brachytherapy dose calculation," Physics in Medicine and Biology, 2014, IOP Publishing, vol. 59, No. 2, pp. 455-464.

\* cited by examiner

METHOD FOR DETERMINING A CONFIGURATION SETTING OF A SOURCE OF IONIZING RADIATION

CROSS-REFERENCE TO RELATED APPLICATIONS

This application is the U.S. national phase of the International Patent Application No. PCT/EP2018/052101 filed Jan. 29, 2018, which claims the benefit of European Application No. 17305111.1 filed Jan. 31, 2017, the entire content of which is incorporated herein by reference.

FIELD

The invention pertains to the field of reducing exposure of practitioners to ionizing radiation in a medical operating room during interventional procedures. In particular, the invention seeks to provide the best configuration setting for a source of ionizing radiation to prevent practitioners and patients from receiving an excessive radiation dose while at the same time ensuring satisfactory imagery of the anatomy of the patient.

BACKGROUND

Minimally invasive medical procedures are becoming increasingly popular due to their effectiveness in reducing patient trauma as well as hospitalization time. These techniques often involve the use of real-time imaging techniques during the procedure. Imaging techniques used during such interventional procedures generally rely on the use of a source of ionizing radiation which exposes both the patient and practitioners evolving in a medical operating room to hazardous radiation doses.

There is a growing concern that ionizing sources of radiation used during such interventional procedures can induce long-term health hazards, especially among practitioners evolving in the medical operating room. It is known that some body parts are particularly sensitive to ionizing radiation (eyes, head, skin, legs, gonads) especially when they are not covered at least by protective clothing. Exposure to ionizing radiation can lead to health hazards such as eye or skin injuries when a threshold dose of ionizing radiation is exceeded. The magnitude of the dose of ionizing radiation received by the body of the patient or a practitioner, or the dose received by at least one body part of the patient or practitioner increases the severity of subsequent negative biological effects. Furthermore, there is also a known stochastic risk associated with exposure to even low levels of ionizing radiation, which can lead to the random occurrence of cancers for example.

For the above reasons, there is a growing need to provide practitioners with tools allowing them to avoid undue exposure to ionizing radiation in a medical operating room.

Document WO 2016/020278 provides a method for estimating the distribution of radiation hazard in a medical operating room, so that the practitioner may adjust his position in order to avoid areas where the radiation hazard is highest. This estimation relies on Monte Carlo type calculations that take into account radiation exposure to ionizing radiation propagating from the source directly to the individual as well as exposure to ionizing radiation scattered by the environment in the medical operating room. The environment considered to compute ionizing radiation includes objects as well as the patient and practitioners evolving in the medical operating room. Radiation hazard is represented in three dimensions enabling practitioners to see which body parts are exposed to the highest levels of ionizing radiation.

Although the teachings of document WO 2016/020278 provide reliable information regarding spatial distribution of radiation hazard, this information is acquired via lengthy computations requiring either several minutes or hours to be completed, so that they cannot be used to provide a real-time picture of the radiation hazard in the context of a movable source of ionizing radiation.

In the context of minimally invasive interventional procedures, the source of ionizing radiation is generally moved in order to provide images of target anatomical structures of the patient necessary for the practitioners to perform the interventional procedure. The source of ionizing radiation is generally a source of X-rays mounted on a robotized angiographic C-arm. Images of an anatomical structure of the patient are acquired from different projection angles of the C-arm with respect to the patient. At the moment, efforts focus on providing the best image of the target anatomical structure and reduce the dose absorbed by the patient in the process. The configuration setting of a source of ionizing radiation are not adapted to take into account the radiation dose absorbed by the practitioners evolving in the medical operating room. However, most interventional procedures involve real time acquisition of several images from different projections which expose the practitioner to radiation hazard. Fluoroscopy-guided interventions are one example of such hazardous interventional procedures.

There is therefore a need to provide a method for determining an appropriate configuration setting for a source of ionizing radiation that can reduce the radiation dose absorbed by a patient and practitioner in a medical operating room during an interventional procedure.

SUMMARY

To overcome the above-listed deficiencies of the prior art, the invention provides a method for determining a configuration setting of a source of ionizing radiation for which a radiation dose absorbed by a patient and at least one practitioner in a medical operating room is reduced during a procedure involving the use of the source, the configuration setting of the source enabling the production of an image of a target anatomical structure of the patient, the method comprising:

prior to the procedure:
/a/ obtaining a model of at least a portion of the medical operating room;
/b/ obtaining a database of maps of simulated propagation and scattering of ionizing radiation in the model of the at least one portion of the medical operating room for different configuration settings of the source; and during the procedure:
/c/ identifying a current position of the at least one practitioner in the medical operating room;
/d/ determining a set of configuration settings of the source enabling the production of the image of the target anatomical structure;
for a configuration setting of the source among the set of determined configuration settings of the source:
/e/ estimating a radiation dose absorbed by a model of at least one body part of the patient and a radiation dose absorbed by a model of at least one body part of the at least one practitioner using the maps from the database;

/f/ determining a combined radiation dose absorbed by the model of at least one body part of the patient and the model of at least one body part of the at least one practitioner; and /g/ outputting a recommended configuration setting of the source among the set of configuration settings of the source, the recommended configuration setting being a configuration setting for which the determined combined radiation dose is reduced.

By obtaining pre-calculated maps of the scattered radiation for different configuration settings of the source, the invention efficiently reduces computation times required to obtain the dose of radiation absorbed by the practitioner from direct and scattered ionizing radiation propagating in the medical operating room. The term "obtaining" can revert to situations in which the database is generated by the person implementing the method of the invention, or to situations in which the database is provided by a third party. Furthermore, the invention advantageously performs, during the procedure and in real time, only a small number of calculations required to determine the radiation dose absorbed by the model of at least one body part of the patient and the model of at least one body part of the practitioner. This efficient reduction of the amount of calculations enables the calculations to be performed in real-time and to provide a recommended configuration setting as the practitioner moves in the medical operating room.

The term "radiation dose" refers both to an average, global radiation dose absorbed over time and an instantaneous radiation dose absorbed by the patient or practitioner. Indeed, the invention can track changes in the ionizing radiation received by body parts of the patient and practitioner in real time, and therefore react when sudden radiation spikes appear.

The invention can be implemented when more than one practitioner is present in the medical operating room.

Step /d/ consisting in determining a set of configuration settings enabling the production of the image of the target anatomical structure can be implemented in many different ways. This set can be determined using an empiric approach (for example, an approach that sets a range of positions and orientations of the source for which an acceptable image quality is to be expected). The subsequent steps can be implemented for a subset of this set of configuration settings (for example when an algorithm seeking a local or global minimum of the combined radiation dose is used, such as a simulated annealing algorithm or any minimization algorithm), or for each of the configuration settings from the determined set. The outputted recommended configuration setting can be either provided to the practitioner who then decides on the following course of action, or can be automatically programmed and set by the source.

According to an embodiment, the method may further comprise:
    operating the source at the recommended configuration setting.

When the source is used at the recommended configuration setting, the radiation dose absorbed by the practitioner and the patient is effectively reduced.

According to an embodiment, the configuration setting may comprise parameters chosen from among: a position of the source with respect to the patient, an orientation of the source with respect to the patient, energy supply of the source affecting intensity of the ionizing radiation emitted by the source.

When the position or orientation of the source with respect to the patient is changed, the spatial distribution of scattered ionizing radiation is modified. A setting that minimizes the dose received by the practitioner given his identified position in the medical operating room can be selected. When the energy supply of the source is changed, the magnitude of the absorbed radiation sources can be modified.

According to an embodiment, the method may further comprise, during the procedure:
    tracking the current position of the at least one body part of the at least one practitioner in the medical operating room;
    repeating steps /d/ through /g/ when the current position of the at least one body part of the at least one practitioner in the medical operating room changes.

Such an approach enables a real-time determination of the most appropriate configuration setting that reduces the radiation dose absorbed by the patient and practitioner. It is for example possible to dynamically change the configuration setting as the practitioner moves in the medical operating room during the procedure, or otherwise suggest a change in the configuration setting and let the practitioner decide on what to do.

According to an embodiment, the method may further comprise, during the procedure:
    tracking changes of a scattering environment in the medical operating room;
    repeating steps /d/ through /g/ when the scattering environment in the medical operating room changes.

Modifications in the position of objects in the medical operating room may have an impact on the spatial distribution of the ionizing radiation in the medical operating room. It is advantageous to have obtained maps at step /b/ for different likely configurations of the scattering environment (for example, for different positions of medical equipment other than the source of ionizing radiation), to take that into account. Furthermore, modifications in the environment can be tracked online and maps of simulated propagation and scattering of ionizing radiation updated in real-time accordingly. By pre-computing scatter maps of a scattering element such as a person or object, it is possible to update the pre-computed maps rapidly by placing the pre-computed maps at the current position of a person or object.

According to an embodiment, the method may further comprise, prior to the procedure:
    defining a position of the patient with the respect to the source;
    adding a model of the patient at the defined position of the patient in the model of the at least one portion of the medical operating room;
    including propagation of radiation absorbed and scattered by the model of the patient in the model of the at least one portion of the medical operating room when obtaining a database of maps of simulated propagation of ionizing radiation.

The position of the patient in the medical operating room can be chosen before the procedure and the patient generally does not move or at least not much during the procedure. However, the patient is an important source of scattered ionizing radiation and calculations associated with this scattering are complex. Providing pre-calculated maps of this scattered radiation reduces computation times of radiation doses absorbed by the patient and the practitioner, and also provides a more accurate value for these doses. The model of the patient, which is then part of the model of the at least one portion of the medical operating room, can be a generic model or a patient-specific one. Patient-specific models provide a more accurate picture of scattered radiation and such models can be computed a few minutes before the procedure for example.

According to an embodiment, the method may further comprise, during the procedure:
- tracking the current position of at least one body part of the patient in the medical operating room;
- repeating steps /d/ through /g/ when the current position of the at least one body part of the patient in the medical operating room changes.

If the patient moves or is moved during the procedure, it is advantageous to take these modifications of the position of patient into account in the model of the patient, to compute a more accurate dose received by the patient or at least one of his body parts. It is also possible to track movements of the patient to update the map of radiation scattered by the patient.

According to an embodiment, the method may further comprise, prior to the procedure:
- defining at least one area in the model of the at least one portion of the medical operating room at a location at which the at least one practitioner is expected to evolve in the medical operating room;
- obtaining the database of maps of simulated propagation and scattering of ionizing radiation for the at least one area only.

By reducing the volume of the space in which radiation propagation is calculated to determine the radiation dose absorbed by the practitioner or at least one of his body parts, the invention further optimizes the speed of the calculations providing absorbed radiation doses. For example, the at least one area can be an area around the head, hands, neck or trunk of the practitioner. No calculations need to be performed outside of the selected area since radiation propagation outside the area does not contribute to the radiation dose absorbed by the practitioner.

In particular, the at least one area may be a surface encompassing a portion of the medical operating room in which the at least one practitioner is expected to evolve, the surface being associated with trajectories and energies of particles from the simulated propagation and scattering of ionizing radiation intersecting the surface.

Maps obtained prior to the procedure contain a multitude of propagation paths for ionizing particles emitted from the source and scattered by the environment (objects, patient and any other source of scattered radiation). However, only a limited number of these particles will interact with the practitioner and contribute to the radiation dose absorbed by his body or one of his body parts. The invention optimizes the number of calculations performed by only keeping the particles having a trajectory which crosses the practitioner when calculating an absorbed radiation dose. The information regarding these particles is stored in a surface, each particle stored in the surface being related to an energy and propagation vector. In some embodiments, the information stored in the surface is statistical information which adds the magnitude of radiation of several particles following a substantially similar propagation path across the surface. This way, the determination of the most appropriate configuration setting can be performed even faster.

According to an embodiment, the surface may be a regular polyhedron.

According to an embodiment, the combined radiation dose can be determined by adding the radiation dose absorbed by the model of the at least one body part of the patient and the radiation dose absorbed by the model of at least one body part of the at least one practitioner, a first weight coefficient being applied to the radiation dose absorbed by the model of the at least one body part of the patient and a second weight coefficient being applied to the radiation dose absorbed by the model of the at least one body part of the at least one practitioner.

The use of different weight coefficients for the dose absorbed by the patient and the practitioner enables a finer tuning of the acceptable dose for both individuals, taking into account the fact that the patient is only rarely exposed to such ionizing radiation whereas the practitioner is subject to such radiation hazard on a regular basis.

According to an embodiment, the method may further comprise:
- selecting the recommended configuration setting corresponding to a configuration setting for which a determined combined radiation dose is reduced below a predetermined threshold.

According to an embodiment, the method may further comprise, during the procedure:
- estimating, for each configuration setting of the source among the set of determined configuration settings of the source, a quality of the image of the target anatomical structure of the patient;
- selecting the recommended configuration setting as being a configuration setting for which the determined combined radiation dose is reduced below a predefined threshold and the quality of the image of the target anatomical structure of the patient is above a predetermined quality threshold.

Image quality is another parameter that can be taken into account when selecting a most suitable configuration setting. By defining a quality threshold and threshold radiation dose, it is possible to give more or less weight to either optimized parameter.

According to an embodiment, the method may further comprise:
- defining a cost function f expressed as:

$$f(C,T,P) = \alpha v(C,P) + \beta h(C,T,P) + \gamma i(C,P)$$

wherein C is a configuration setting of the source, T is the current position of the at least one practitioner, P represents patient parameters comprising at least the position of the patient in the medical operation room, v represents the radiation dose absorbed by the at least one body part of the patient, h represents the radiation dose absorbed by the at least one body part of the at least one practitioner, i represents the quality of the image of the target anatomical structure of the patient and $\alpha$, $\beta$, $\gamma$ are weight coefficients,
- selecting the recommended configuration which minimizes cost function f.

The invention also pertains to a computer program product comprising programs instructions, the computer program product being loadable into a data-processing device and adapted to cause the data-processing unit to carry out steps /a/ through /g/ described above when the computer program is run by the data-processing device.

BRIEF DESCRIPTION OF THE DRAWINGS

The method of the invention will be better understood by reading the detailed description of exemplary embodiments presented below. These embodiments are illustrative and by no means limitative. They are provided with the appended figures and drawings on which.

For the sake of clarity, the dimensions of features represented on these figures and drawings may not necessarily correspond to the real-size proportions of the corresponding elements. Like reference numerals on the figures and drawings correspond to similar elements or items.

DETAILED DESCRIPTION

The invention seeks to optimize configuration settings of a source of ionizing radiation in order to at least reduce a radiation dose absorbed by a practitioner while at the same time also preserving the patient from exposure to excessive radiation doses. The strategy used to find this optimized configuration setting can vary, but is chosen to allow the process to occur in quasi real time, that is to say within seconds, so that a practitioner does not have to interrupt his interventional procedure, which could compromise the health of the patient and disturb the practitioner.

Figure 1:
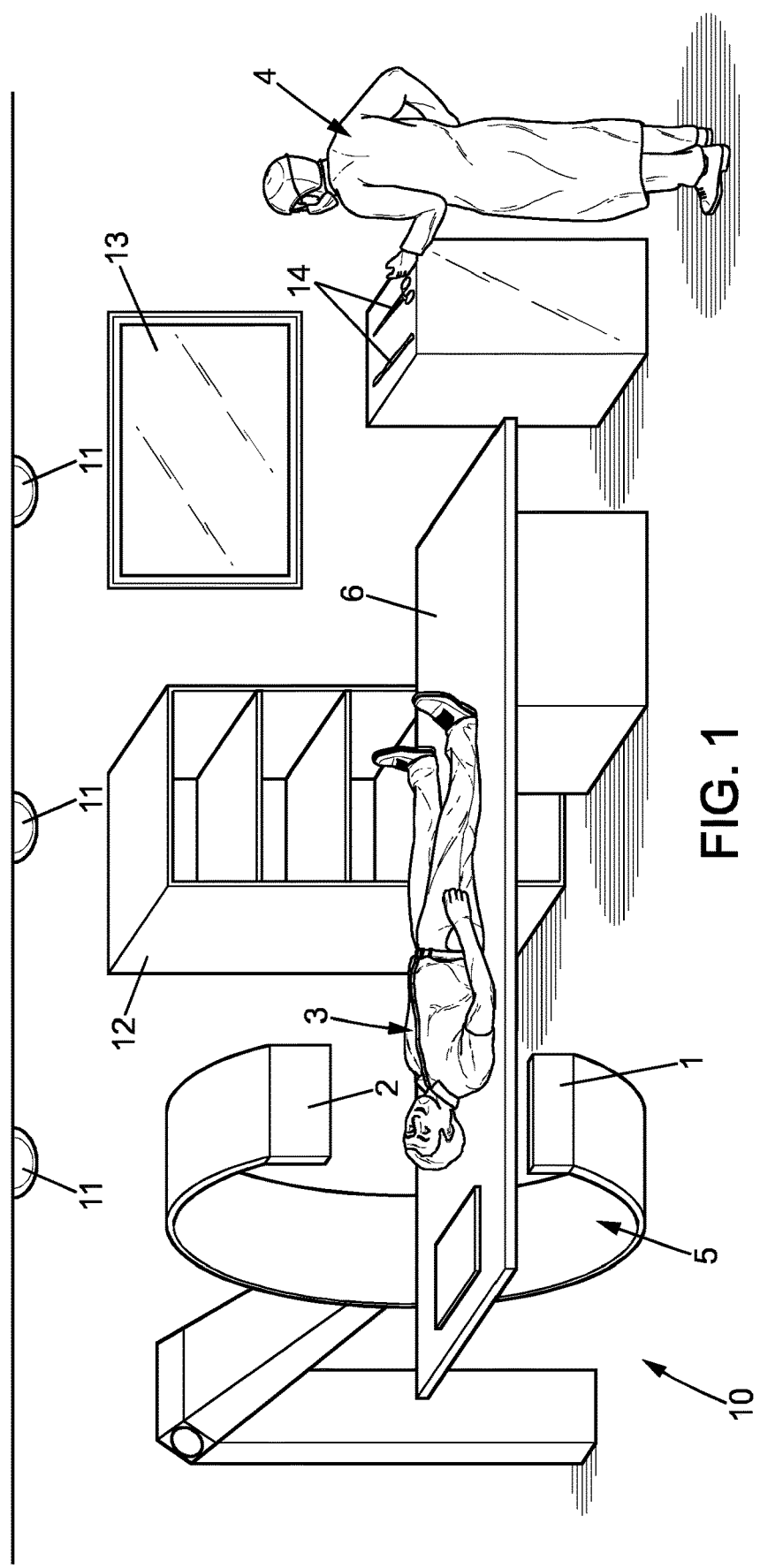
FIG. 1 is a schematic representation of a three-dimensional environment comprising a source of ionizing radiation.

An example of a medical operation room 10 comprising a source of ionizing radiation 1 is illustrated on FIG. 1. The source is part of an angiographic C-arm 5 which also comprises a detector 2. A patient 3 generally lies between the source and the detector 2 on a medical operation table 6. At least one practitioner 4 evolves in the medical operating room 10 during an interventional procedure. There can be more than one practitioner in the medical operating room 10.

The environment surrounding the source of ionizing radiation 1 comprises several elements capable of scattering radiation in all directions. Scattering elements can for example comprise medical appliances and furniture 12, 13, 14, the patient himself 3 and the at least one practitioner 4.

Sensors and cameras 11 can be placed in the medical operating room to locally monitor the magnitude of radiation at specific locations in the medical operating room 10, and track the position of scattering elements, the patient 3 and the at least one practitioner 4. Measurements from sensors may also be used to calibrate or validate the simulations of propagated and scattered radiation, or can be used instead of simulated values in parts of the medical operating room if applicable.

During an interventional procedure, the source of ionizing radiation 1 and the detector 2 are placed around the patient 3 so that a target anatomical structure of the patient can be imaged. The procedure may require repositioning the source of ionizing radiation 1 to image different body parts of the patient and the at least one practitioner 4 generally moves in the medical operating room to perform his tasks. These changes in the configuration setting of the source and the position of the practitioner require a fast computation of radiation doses to which the practitioner is exposed.

Although image quality of the target anatomical structure is traditionally the main parameter taken into consideration today for repositioning a source of ionizing radiation, it has been observed, in the context of the invention, that slight changes in the configuration setting of the source do not necessarily have a significantly negative impact on image quality, but can have a noticeable impact on the distribution of radiation in the medical operating room 10. This observation and the extent of acceptable changes in the configuration parameters which enable maintaining a decent image quality depend on the nature of the imaged anatomical structure. For example, only small angular changes are acceptable during vascular procedures; in which visibility of a vascular structure can disappear even with small changes in the orientation of the source.

The invention seeks to rely on this observation to find an acceptable compromise between image quality and radiation doses received by the patient 3 and the at least one practitioner 4. One constraint arising from the context of an interventional procedure is that this compromise has to be found in quasi real-time, that is to say within seconds.

Figure 2:
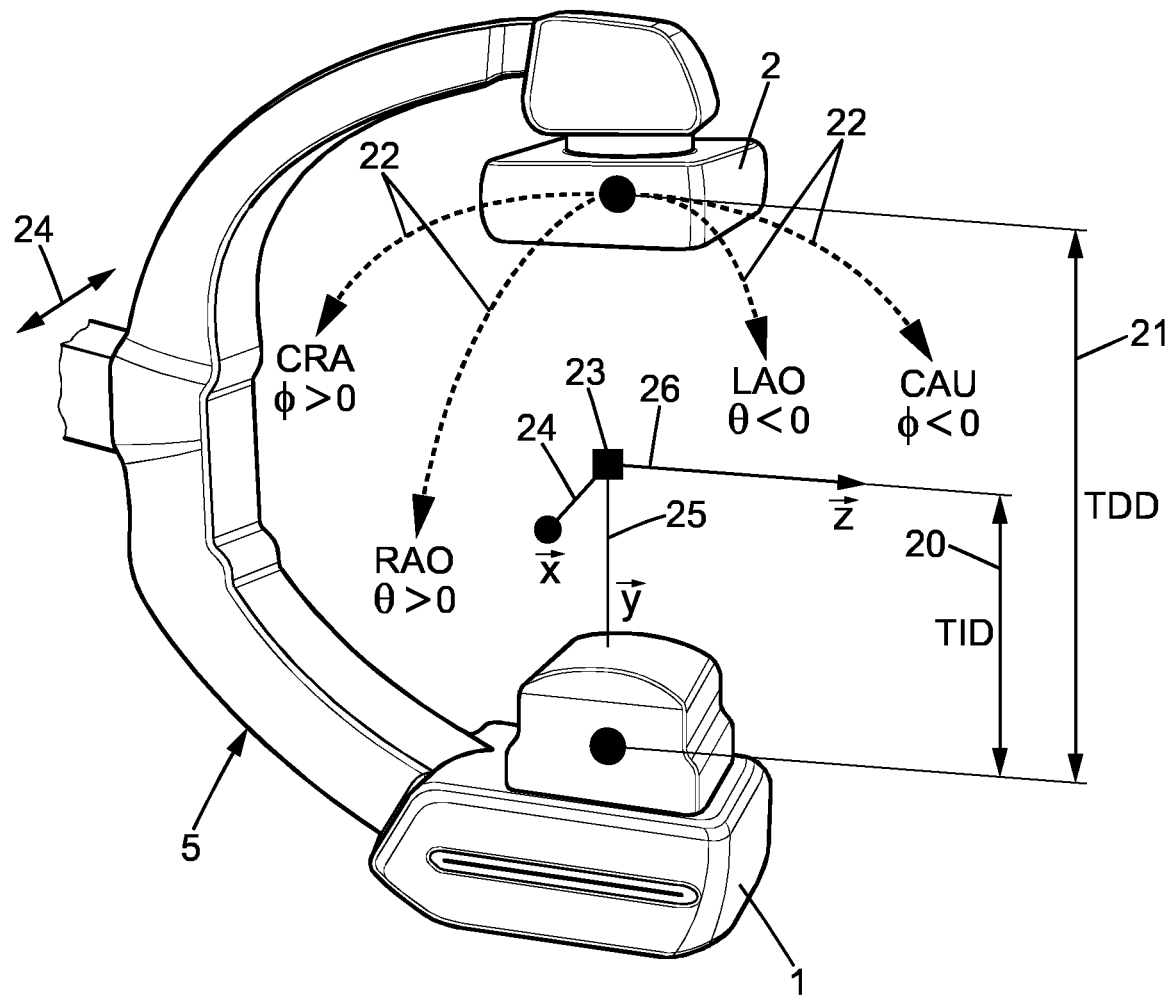
FIG. 2 is a schematic representation of a source of ionizing radiation in the form of a C-arm and its possible translational and rotational degrees of freedom.

FIG. 2 illustrates an angiographic C-arm 5 comprising a source 1 and a detector 2. The C-arm can be animated along different directions in three dimensions and rotated around the patient to obtain a desired image of an anatomical structure. Isocenter 23 represents the focal point of the anatomical structure to be imaged. Isocenter 23 generally is located somewhere in the body of the patient. Lateral translations of the source of ionizing radiation along axis x, 24, or y, 25 or z, 26 are possible. The distance 20 between isocenter 23 and the source of ionizing radiation 1, also called "Tube to isocenter" or TID is also an adjustable parameter of the C-arm. The distance 22 between the source of ionizing radiation 1 and the detector 2, also called "Tube to detector distance" or TDD can also be adjusted. The source of ionizing radiation 1 can also be tilted along two angles $\theta$ (right/left anterior oblique or RAO, LAO) and $\phi$ (caudal/cranial orientation or CAU, CRA), as illustrated on FIG. 2, to change the orientation 22 of the source with respect to the patient.

These degrees of freedom enable the production of many different images with different levels of detail of anatomical structures of the patient 3.

Another parameter that can be adjusted is the supply of energy to the source of ionizing radiation 1, which affects intensity of the ionizing radiation emitted by the source.

The configuration setting of the source of ionizing radiation 1 can comprise the above described position and orientation of the source and/or energy supply of the source.

When a target anatomical structure of the patient is identified, a first configuration setting $C_{nom}$ is selected. This configuration setting does not reduce radiation doses absorbed by the at least one practitioner 4, nor the dose absorbed by the patient in most cases. Parameters of configuration setting $C_{nom}$ can be changed without losing too much image quality. A typical range of acceptable modifications of angles $\theta$ and $\phi$ lies within +/−10°, and generally depends on the targeted anatomical structure. A certain tolerance on modification of energy supply and translation along axis x, y, z and modification of distances TID and TDD is also acceptable. Configuration settings for which some of these parameters are changed without losing considerable image quality form a set S of configuration settings of the source enabling the production of the image of the target anatomical structure.

The invention seeks to find one configuration setting among set S which reduces at least radiation doses absorbed by at least one body part of the at least one practitioner 4 and at least one body part of the patient 3. It is to be further noted that the method of the invention can also be used to reduce the radiation dose absorbed by a patient when no practitioner is present (typically, when the practitioner moves away to a safe location from the source of ionizing radiation 1).

Figure 3:
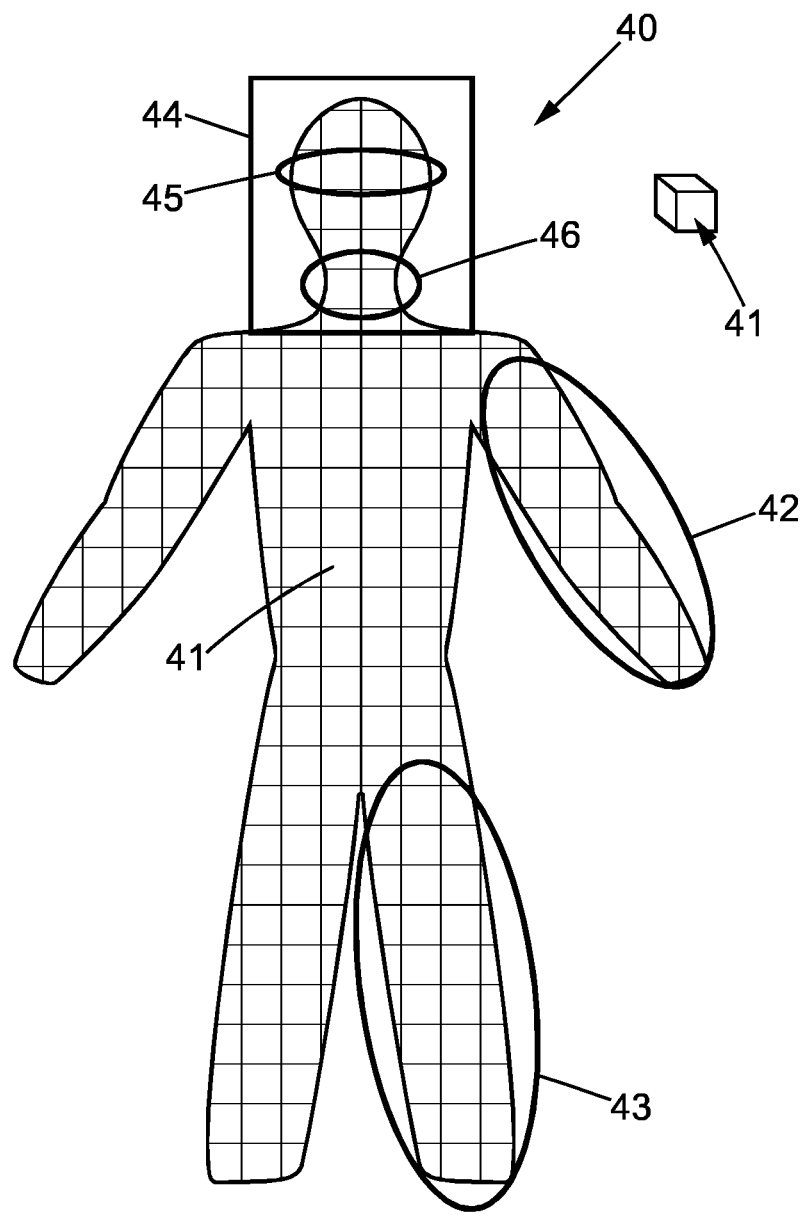
FIG. 3 is a schematic representation of a model of an individual with voxels.

To select an appropriate configuration setting from set S, the invention computes radiation doses absorbed by the patient and practitioner for different configuration settings from set S. To do so, the patient 3 and the at least one practitioner 4 are modeled as phantoms, such as the one illustrated on FIG. 3. The body 40 of an individual is decomposed into voxels 41, and different body parts such as legs 43, arms 42, the head 44, eyes 45 or neck 46 are identified.

Depending on which body part is monitored, the corresponding voxels 41 are intersected with the trajectory of particles emitted from the source of ionizing radiation 1, whether they travel directly from the source to the voxel 41 or are scattered by the environment surrounding the source, by the body of the patient 3, the body of the at least one practitioner 4 or another voxel 41 of the patient 3 or of the at least one practitioner 4.

Simulations of the trajectory and scattering of particles from the source is a lengthy process and can hardly be implemented within seconds, in quasi real-time.

Since the arrangement of the medical operating room 10 and most sources of scattered radiation in the room are known, as well as all the possible configuration settings of the source, it is possible to obtain maps of the propagated and scattered radiation in the medical operating room 10 before the interventional procedure. Pre-calculated maps provide energies and trajectories of a multitude of particles emitted from the source of ionizing radiation 1 operated at different configuration settings. These maps are generated in a model of at least a portion of the medical operating room 10, and can also include a model of the patient 3 placed in the model of the at least one portion of the medical operating room 10 at a position at which the patient 3 is due to be on the medical operation table 6. That way, the patient 3 can be considered as a source of scattering radiation and improve accuracy of the method to compute absorbed radiation doses.

Alternatively, it is also possible to track changes in the medical operating room affecting the profile of scattered radiation during the procedure.

These pre-calculated maps save a lot of computation time, and reduce real-time calculations to the calculation of radiation doses absorbed by either some body part or body parts of the patient 3 and at least one practitioner 4 or their whole bodies.

During the procedure, the at least one practitioner evolves in the medical operating room 10 and his current position is tracked in real time.

Wherever the at least one practitioner 4 is in the room, the trajectories and energy of particles of ionizing radiation in the room are already stored in the pre-calculated maps. The dose absorbed by the practitioner is computed by identifying the current position of the practitioner and by intersecting voxels 41 of the model of the body of the practitioner with the particles stored in the maps for different configuration settings of the source.

A similar process computes the dose absorbed by the patient 3.

The calculation can further be enhanced by monitoring possible movements of the patient during the procedure, or changes of scattering objects in the environment.

Figure 4:
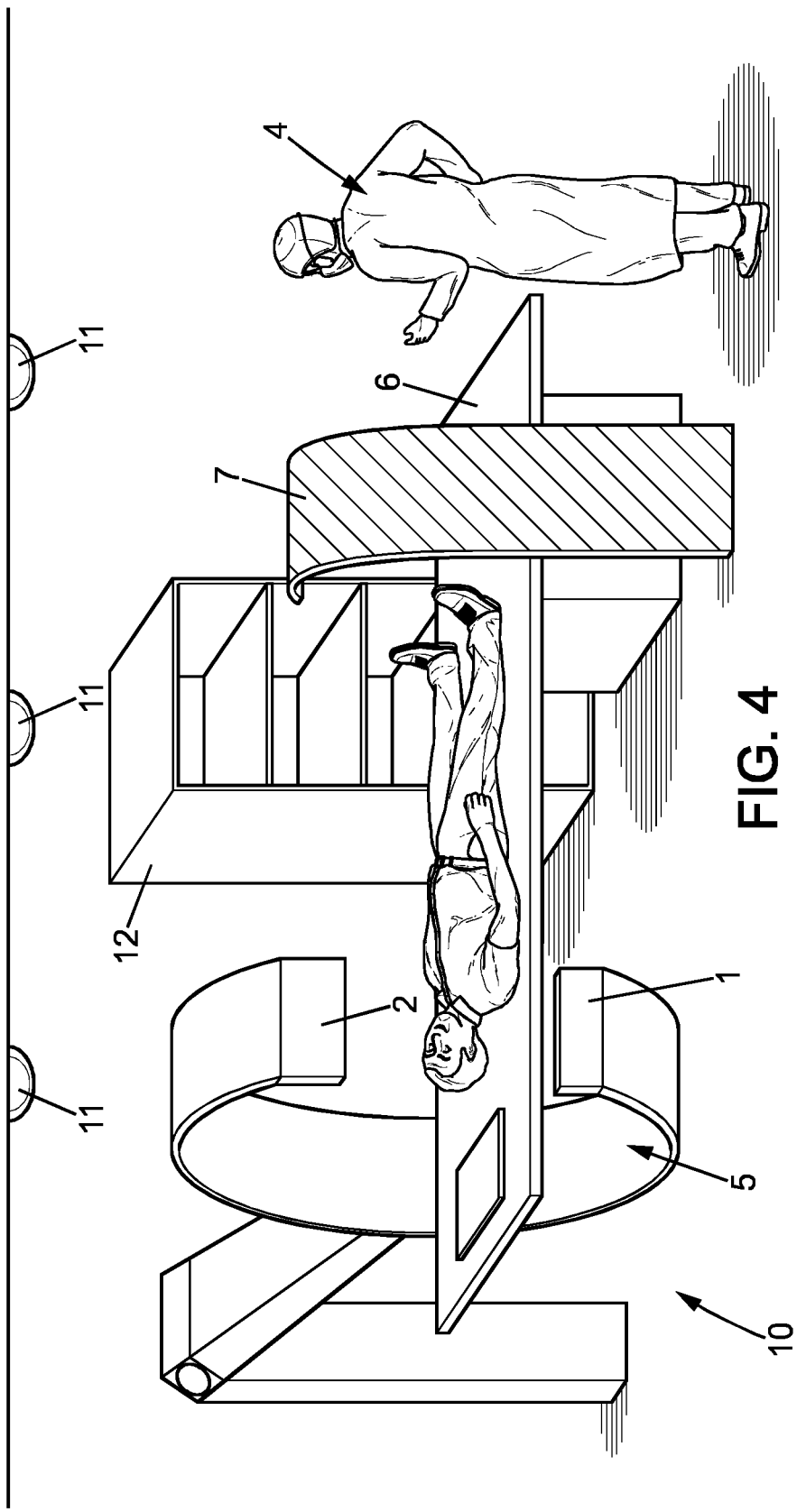
FIG. 4 is a schematic representation of a surface selected around the practitioner to compute the radiation dose absorbed by the practitioner using particles stored in said surface in pre-calculated radiation propagation and scatter maps.

FIG. 4 provides one illustration of a further improvement reducing the amount of calculations required to compute the radiation dose absorbed by the at least one practitioner 4. In FIG. 4, the model of the at least one portion of the medical operating room 10 is reduced to an area 7, which is a surface selected in the vicinity of a body part of the at least one practitioner 4 and around the patient or any scattering element of the environment. This surface can for example be a polyhedron, a sphere or any other appropriate surface in the vicinity of the practitioner. Instead of taking all the particles stored in the maps into account, the radiation dose absorbed by the practitioner is calculated using only those particles stored in the maps which intersect area 7. In FIG. 4 area 7 is a surface in front of the at least one practitioner 4, and stores information regarding particles emitted from the patient and scattering elements in the environment having a trajectory which cross the surface and are oriented towards the practitioner.

Particles stored in this surface are associated with an energy and propagation vector. To further simplify the calculation of the absorbed radiation dose, particles can be grouped together and their energy added up when they have substantially similar directions (that is a direction that typically differs by less than 5°).

Of course, it is possible to define an area 7 and surface having any shape, or define several surfaces to determine radiation doses absorbed by different body parts of the practitioner.

The radiation dose absorbed by the patient 3 is computed in a similar way.

Due to the high speed at which these calculations can be performed (within seconds), the radiation dose that is calculated can be both an instantaneous radiation dose, accounting for sudden radiation spikes, as well as a cumulated radiation dose accounting for all radiation absorbed over the course of the procedure.

The choice of a new configuration setting can be made by minimizing a cost function f, such that:

$$f(C,T,P)=\alpha v(C,P)+\beta h(C,T,P)+\gamma i(C,P)$$

wherein C is a configuration setting of the source, T is the current position of the at least one practitioner 4, P represents patient parameters comprising at least the position of the patient in the medical operation room 10, v represents the radiation dose absorbed by the at least one body part of the patient 3, h represents the radiation dose absorbed by the at least one body part of the at least one practitioner 4, i represents the quality of the image of the target anatomical structure of the patient and α, β, γ are weight coefficients.

This cost function can further take into account a current position of the patient in term v, as briefly discussed above.

Weighing term α, β can be used to tune which type of radiation is deemed acceptable for the patient 3 and the at least one practitioner 4. The patient can absorb a higher radiation dose than the practitioner, the latter being exposed to lower levels of ionizing radiation on a regular basis. For the practitioner, a configuration setting which leads to an absorbed radiation dose "as low as reasonably achievable" (also referred to as ALARA in common literature) is sought.

As seen on the above expression of cost function f, it is possible to add a parameter i taking into account the quality of the image of the target anatomical structure. Indeed, a practitioner may require a certain image resolution or contrast quality, or visibility of a target anatomical structure for example and can set image quality as being a parameter of the method selecting an improved configuration setting of the source.

Image quality can for example quantitatively be assessed by simulating an image using an a priori model of the patient. That way, anatomical structure size, contrast, image resolution can be provided for each configuration setting that is used in the method of the invention.

The invention can further comprise an option which identifies a more suitable position for the practitioner than his current position if one configuration setting comprises a zone in the medical operating room 10 with a particularly low level of ionizing radiation.

Cost function f can be minimized using all sorts of algorithms. One possibility is to use a global minimization algorithm such as simulated annealing or probing each configuration setting from the set S individually to find the lowest value of cost function f.

Such an approach can lead to lengthy computations and a gradient descent approach is preferred. The gradient descent approach tests configuration settings with slightly varying parameters at each iteration loop until a stop condition is reached. This stop condition can for example be a fixed number of iterations (test of different configuration settings) or a relative reduction in the value of cost function (for example, a certain reduction in the combined radiation dose of the patient and practitioner or a relative percentage reduction of the value of the cost function such as a 25% reduction).

A gradient descent approach provides a local minimum for the cost function which can be deemed acceptable, especially if this approach saves computation time.

As a result of this minimization step, the method outputs a recommended configuration setting $C_{opt}$. Either this information is provided to the practitioner who decides whether to accept the new setting $C_{opt}$ or not, or the recommended configuration setting is provided to a control unit which automatically orders the source of ionizing radiation 1 to operate at $C_{opt}$.

Figure 5:
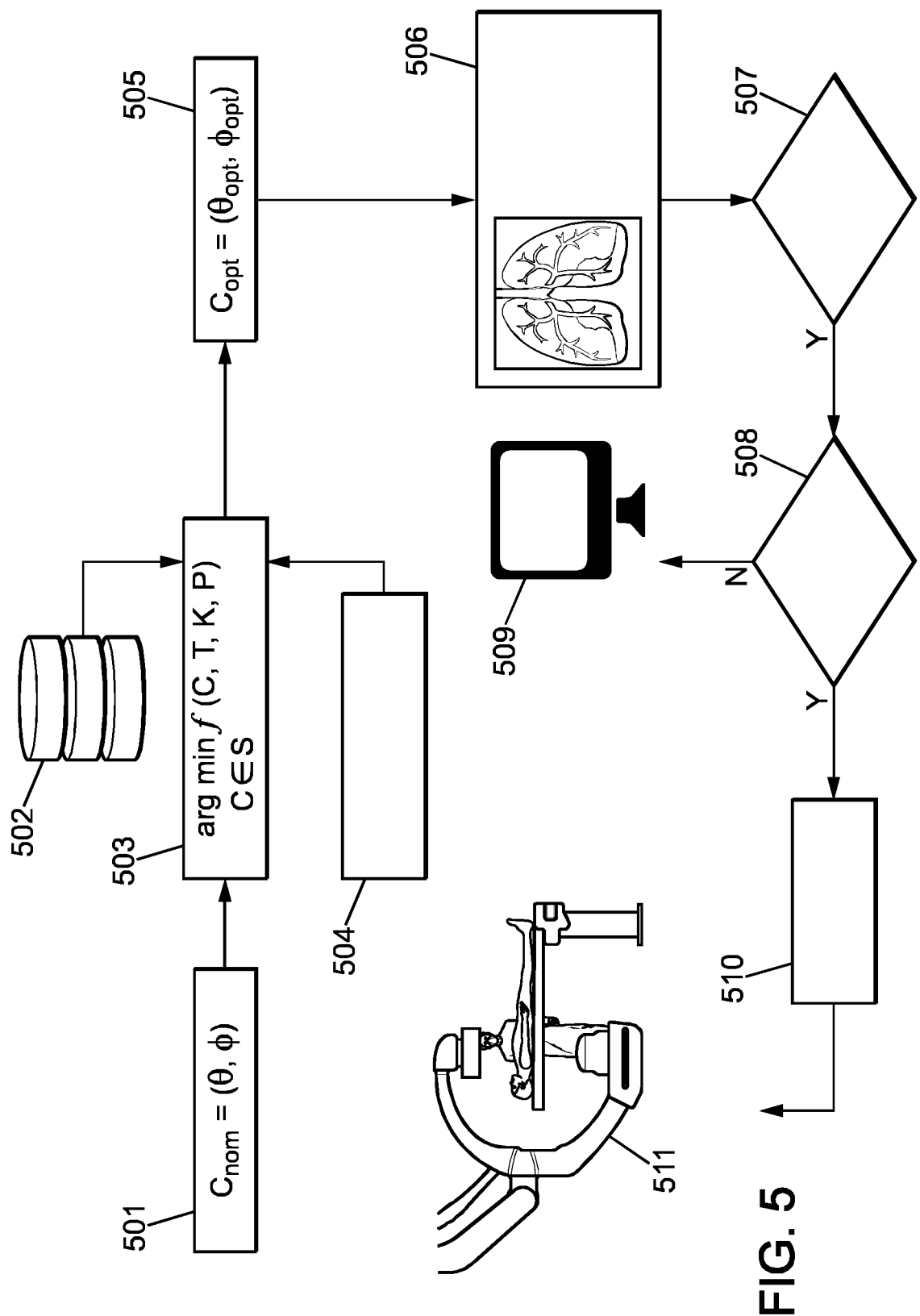
FIG. 5 is a flow chart showing possible steps for implementing the method of the invention.

FIG. 5 is a flowchart providing one example embodiment of the method described above. At a first step 501 a starting configuration setting $C_{nom}$ for the source is selected. At a step 502, which occurs prior to the procedure, a database of maps of radiation propagation and scattering in at least a portion of the medical operating room 10 is performed. At step 504, conditions for defining a cost function f can be input (such as for example radiation threshold levels, image quality threshold). At step 503 cost function f is minimized using an appropriate minimization algorithm.

At step 505, a recommended configuration setting for the source is output. At step 506, a simulated image of the anatomical structure is provided along with information regarding radiation exposure. This step is optional and serves to inform the practitioner on the risk associated with the recommended configuration setting, possibly suggesting a new position for the practitioner.

At step 507, approval by the practitioner or by a machine is requested. If no approval is reached, the method starts over or keeps the current configuration setting. If approval is given, the method checks at step 508 whether an application programming interface is available to order the source to operate at the new configuration setting. If no such application is present the new configuration setting is provided to the practitioner so that he may reposition the source if he so wishes. If such an application does exist, inverse kinematics is performed at step 510 to define how to reposition, reorient and resupply with energy the source of ionizing radiation 1. At step 511, the source is ordered at the new configuration setting.

Figure 6:
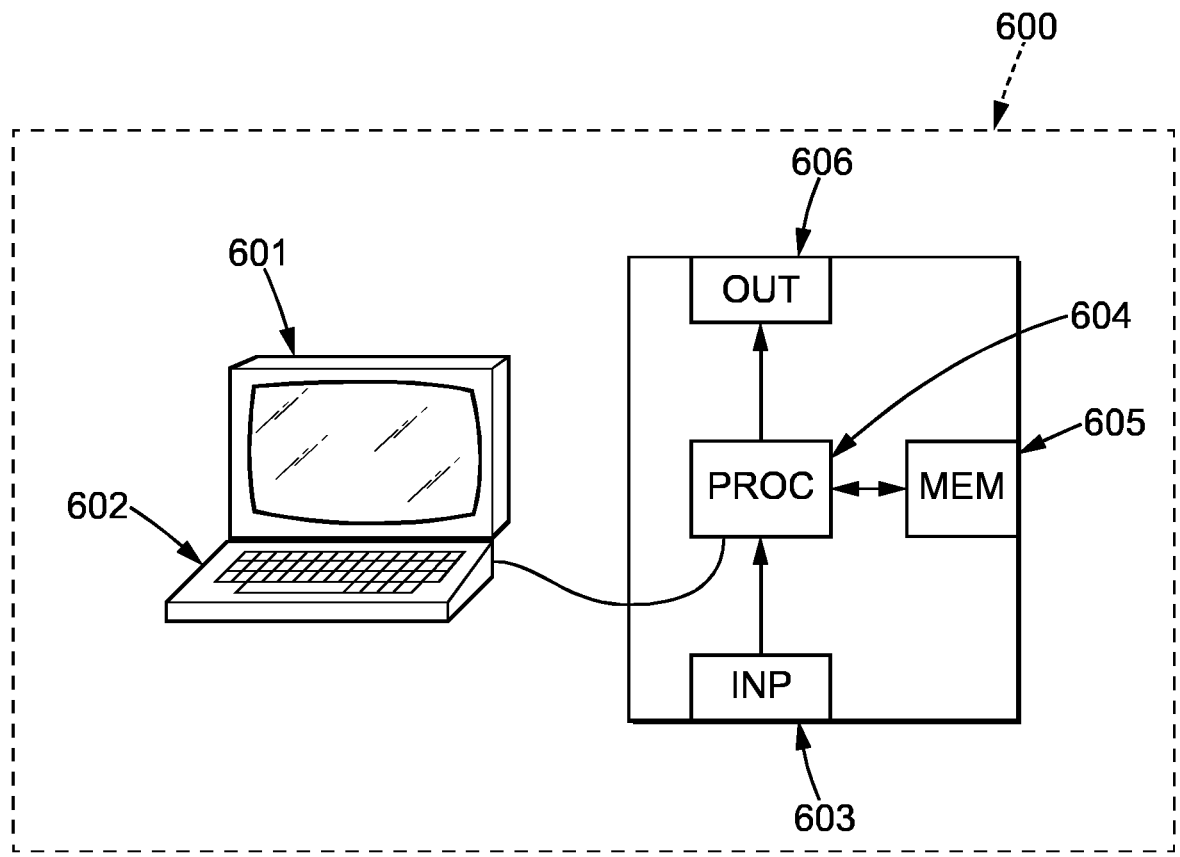
FIG. 6 is a possible embodiment for a computer system adapted for implementing the method of the invention.

FIG. 6 is a possible embodiment for a computer system configured for implementing the above-described method.

The computer system 600 comprises a computer, this computer comprising a memory 605 to store program instructions loadable into a circuit and adapted to cause circuit 604 to carry out the steps of the present invention when the program instructions are run by the circuit 604.

The memory 605 may also store data and useful information for carrying the steps of the present invention as described above.

The circuit 604 may be for instance:
a processor or a processing unit adapted to interpret instructions in a computer language, the processor or the processing unit may comprise, may be associated with or be attached to a memory comprising the instructions, or
the association of a processor/processing unit and a memory, the processor or the processing unit adapted to interpret instructions in a computer language, the memory comprising said instructions, or
an electronic card wherein the steps of the invention are described within silicon, or
a programmable electronic chip such as a FPGA chip (for «Field-Programmable Gate Array»).

This computer comprises an input interface 603 for the reception of data used for the above method according to the invention (such as for example, radiation thresholds or image quality thresholds) and an output interface 606 for providing a recommended configuration setting of the source of ionizing radiation.

To ease the interaction with the computer, a screen 601 and a keyboard 602 may be provided and connected to the computer circuit 604.

The above described method provides fast and accurate estimates of the radiation dose absorbed by a patient and practitioner, in quasi-real time, and finds an improved configuration setting which limits this dose without losing considerable image quality during an interventional procedure.

Radiation doses computed using the advantageous simplifications described above to limit the number of calculations performed during an interventional procedure were compared to results obtained using full Monte Carlo type simulations. It has been shown that results agree with less than 5% differences between the two methods, which proves that the invention successfully overcomes the challenge of computation times without losing accuracy.

The invention claimed is:

1. A method for determining a configuration setting of a source of ionizing radiation for which a radiation dose absorbed by a patient and at least one practitioner in a medical operating room is reduced during a procedure involving the use of the source, the configuration setting of the source enabling the production of an image of a target anatomical structure of the patient, the method comprising:
prior to the procedure, the acts of:
/a/ obtaining a model of at least a portion of the medical operating room;
/b/ obtaining a database of pre-calculated maps of simulated propagation and scattering of ionizing radiation in the model of the at least one portion of the medical operating room for different configuration settings of the source; and
during the procedure, the acts of:
/c/ identifying a current position of the at least one practitioner in the medical operating room;
/d/ determining a set of configuration settings of the source including at least one projection angle enabling the production of the image of the target anatomical structure;

for a configuration setting of the source among the set of determined configuration settings of the source:

/e/ estimating a radiation dose absorbed by a model of at least one body part of the patient and a radiation dose absorbed by a model of at least one body part of the at least one practitioner using the pre-calculated maps from the database;

/f/ determining a combined radiation dose absorbed by the model of the at least one body part of the patient and the model of the at least one body part of the at least one practitioner; and /g/ outputting a recommended configuration setting of the source among the set of configuration settings of the source, the recommended configuration setting being a configuration setting for which the determined combined radiation dose is reduced.

2. The method according to claim 1, further comprising the act of:

operating the source at the recommended configuration setting.

3. The method according to claim 1, wherein the configuration setting comprises parameters chosen from among: a position of the source with respect to the patient, an orientation of the source with respect to the patient, energy supply of the source affecting intensity of the ionizing radiation emitted by the source.

4. The method according to claim 1, further comprising, during the procedure, the acts of:

tracking the current position of the at least one body part of the at least one practitioner in the medical operating room;

repeating steps /d/ through /g/ when the current position of the at least one body part of the at least one practitioner in the medical operating room changes.

5. The method according to claim 1, further comprising, during the procedure, the acts of:

tracking changes of a scattering environment in the medical operating room;

repeating steps /d/ through /g/ when the scattering environment in the medical operating room changes.

6. The method according to claim 1, further comprising, prior to the procedure, the acts of:

defining a position of the patient with the respect to the source;

adding a model of the patient at the defined position of the patient in the model of the at least one portion of the medical operating room;

including propagation of radiation absorbed and scattered by the model of the patient in the model of the at least one portion of the medical operating room when obtaining a database of maps of simulated propagation of ionizing radiation.

7. The method according to claim 1, further comprising, during the procedure, the acts of:

tracking the current position of the at least one body part of the patient in the medical operating room;

repeating steps /d/ through /g/ when the current position of the at least one body part of the patient in the medical operating room changes.

8. The method according to claim 1, further comprising, prior to the procedure, the acts of:

defining at least one area in the model of the at least one portion of the medical operating room at a location at which the at least one practitioner is expected to be located in the medical operating room;

obtaining the database of maps of simulated propagation and scattering of ionizing radiation for the at least one area only.

9. The method according to claim 8, wherein the at least one area is a surface encompassing a portion of the medical operating room in which the at least one practitioner is expected to be located, the surface being associated with trajectories and energies of particles from the simulated propagation and scattering of ionizing radiation intersecting the surface.

10. The method according to claim 9, wherein the surface is a regular polyhedron.

11. The method according to claim 1, wherein the combined radiation dose is determined by adding the radiation dose absorbed by the model of the at least one body part of the patient and the radiation dose absorbed by the model of the at least one body part of the at least one practitioner, a first weight coefficient being applied to the radiation dose absorbed by the model of the at least one body part of the patient and a second weight coefficient being applied to the radiation dose absorbed by the model of the at least one body part of the at least one practitioner.

12. The method according to claim 1, further comprising, the act of:

selecting the recommended configuration setting corresponding to a configuration setting for which a determined combined radiation dose is reduced below a predetermined threshold.

13. The method according to claim 1, further comprising, during the procedure, the acts of:

estimating, for each configuration setting of the source among the set of determined configuration settings of the source, a quality of the image of the target anatomical structure of the patient;

selecting the recommended configuration setting as being a configuration setting for which the determined combined radiation dose is reduced below a predefined threshold and the quality of the image of the target anatomical structure of the patient is above a predetermined quality threshold.

14. The method according to claim 1, further comprising, the acts of:

defining a cost function f expressed as:

$$f(C,T,P) = \alpha v(C,P) + \beta h(C,T,P) + \gamma i(C,P)$$

wherein C is a configuration setting of the source, T is the current position of the at least one practitioner, P represents patient parameters comprising at least the position of the patient in the medical operation room, v represents the radiation dose absorbed by the at least one body part of the patient, h represents the radiation dose absorbed by the at least one body part of the at least one practitioner, i represents the quality of the image of the target anatomical structure of the patient and $\alpha, \beta, \gamma$ are weight coefficients, selecting the recommended configuration which minimizes cost function f.

15. A non-transitory computer-readable medium comprising instructions stored thereon, which when executed by a data-processing device configures the data-processing device to carry out acts /a/ through /g/ of claim 1.

* * * * *